(12) United States Patent
Papanek et al.

(10) Patent No.: US 8,562,342 B2
(45) Date of Patent: Oct. 22, 2013

(54) ANGLES HOSE CONNECTION FOR DENTAL HANDPIECE

(75) Inventors: Tom Papanek, Lake Forest, IL (US); Gene Novak, Deerfield, IL (US); Don Heil, Lake Villa, IL (US); Bret Beane, Palatine, IL (US)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 12/319,799

(22) Filed: Jan. 12, 2009

(65) Prior Publication Data

US 2009/0269717 A1 Oct. 29, 2009

Related U.S. Application Data

(63) Continuation of application No. 11/755,866, filed on May 31, 2007, now abandoned.

(60) Provisional application No. 60/803,674, filed on Jun. 1, 2006.

(51) Int. Cl.
*A61C 17/00* (2006.01)
*A61C 17/02* (2006.01)
*A61C 1/08* (2006.01)

(52) U.S. Cl.
USPC ............................................. 433/126; 433/82

(58) Field of Classification Search
USPC ............... 433/126, 80, 81, 89, 114–115, 125, 433/133, 141, 82, 29–31; 239/587.3–587.5, 239/587.1; 285/58, 184, 261, 275, 279, 285/280, 281
See application file for complete search history.

(56) References Cited

U.S. PATENT DOCUMENTS

| 1,688,136 | A | * | 10/1928 | Chayes et al. | 279/76 |
|---|---|---|---|---|---|
| 3,612,408 | A | * | 10/1971 | Holleman | 239/587.3 |
| 4,035,004 | A | * | 7/1977 | Hengesbach | 285/146.1 |
| 4,075,761 | A | * | 2/1978 | Behne et al. | 433/85 |
| 4,088,348 | A | * | 5/1978 | Shemtov | 285/184 |
| 4,177,564 | A | * | 12/1979 | Flatland | 433/82 |
| 4,697,742 | A | * | 10/1987 | Schnipke | 239/587.4 |
| 5,346,489 | A | * | 9/1994 | Levy et al. | 606/15 |
| 5,476,379 | A | * | 12/1995 | Disel | 433/29 |
| 5,505,737 | A | | 4/1996 | Gosselin | |
| 5,716,210 | A | * | 2/1998 | Novak | 433/82 |
| 5,967,779 | A | * | 10/1999 | Brassil et al. | 433/88 |

(Continued)

FOREIGN PATENT DOCUMENTS

WO WO 2007/143071 12/2007

*Primary Examiner* — Yogesh Patel
(74) *Attorney, Agent, or Firm* — David A. Zdurne; Douglas J. Hura; Leana Levin (57) ABSTRACT

A dental handpiece having a distal end including an attachment for assembly of a removable workpiece and a handpiece body intermediate a proximal end and the distal end. The handpiece extends in a substantially axial direction. A coupler is included having a cylinder portion and a supply-end portion, the cylinder portion being assembled into the handpiece extending in the axial direction toward the distal end. The cylinder portion includes at least one seal that interfaces with an interior of the body so as to isolate a portion of the body interior into at least one distinct chamber. The supply-end portion of the coupler extends from the proximal end of the handpiece body at an angle from the axis. The supply-end portion also includes a plurality of outlets, the at least one distinct chamber in fluid communication with one of the outlets of the plurality of outlets.

11 Claims, 6 Drawing Sheets

(56) References Cited

U.S. PATENT DOCUMENTS

| | | | |
|---|---|---|---|
| 6,106,287 A * | 8/2000 | Yates | 433/82 |
| 7,001,391 B2 | 2/2006 | Estes et al. | |
| 7,011,661 B2 | 3/2006 | Riedel et al. | |
| 2002/0151902 A1 | 10/2002 | Riedel et al. | |
| 2003/0023256 A1 | 1/2003 | Estes et al. | |
| 2003/0163134 A1 | 8/2003 | Riedel et al. | |
| 2004/0122460 A1 | 6/2004 | Shores et al. | |
| 2005/0116578 A1 | 6/2005 | Fleury et al. | |
| 2005/0161538 A1 * | 7/2005 | Cattaneo et al. | 239/587.4 |
| 2008/0003537 A1 | 1/2008 | Papanek | |

* cited by examiner

ANGLES HOSE CONNECTION FOR DENTAL HANDPIECE

FIELD OF THE INVENTION

The present invention relates generally to a dental handpiece having an angled coupling between the handpiece body and the flexible supply connection.

BACKGROUND OF THE INVENTION

Dental handpieces typically include a handpiece body, a coupler and a flexible supply connection. The handpiece includes a proximal end, a distal end and a body intermediate the proximal and distal end, the proximal end, the distal end and the handpiece body oriented in a substantially axial direction. An outer surface of the body is molded to be an ergonomic gripping area is so that the dental professional can comfortably grip the handpiece. The distal end has a head onto which a removable workpiece, such as a burr or a prophy-angle is attached. A coupler is assembled axially to the handpiece body, the coupler having a supply-end portion and a cylinder portion projecting from the supply-end portion. The cylinder portion of the coupler, which includes one or more diametral portions, extends in the axial direction into the handpiece body toward the distal end. The supply-end portion is positioned at the proximal end of the handpiece, and may project outward from the proximal end of the handpiece in a direction opposite the distal end. The supply-end portion usually is configured in accordance with an industry standard, here ISO 9168, so as to provide a substantially uniform attachment configuration with the flexible supply connection, the supply connection usually including a hose. The coupler may be molded into the handpiece so as to be integral with it, or it may be a separate, distinct piece removably attached to the handpiece. By integral is meant that the coupler is molded into the handpiece so that it cannot be readily removed from the handpiece, even though the coupler may be a separate component. The coupler usually is adapted to mate with a quick release feature of the flexible supply connection to allow the user to easily attach and remove the handpiece/coupler combination from the flexible supply connection.

As the handpiece requires a supply of air, water and in some cases, a supply of electricity, the coupler at the proximal end of the handpiece facilitates the supply of the required resources from the flexible supply connection. The coupler includes seals typically positioned on its cylindrical portion to isolate water, air and optional electrical power that may be provided. The flexible supply connection typically is a flexible hose that attaches to the coupler. The hose provides air, water and electricity to the handpiece through the coupling. A flexible supply end is typically affixed to the flexible supply, such as a hose connector using a threaded ring, configured to mate with the coupler supply end, and thus also meets the applicable ISO standard. The coupler may be a swivel coupler that rotates as the handpiece is moved by the dental professional so that the rotational motion of the coupler and flexible supply connection is substantially independent that of the handpiece, thereby providing the dental professional with some freedom of movement as he/she manipulates the handpiece in the patient's mouth. Couplers are typically a proprietary design which only fits the handpieces of one manufacturer. More specifically, since the supply end portion of the coupler is made in accordance with an industry standard that allows it to mate with the flexible supply connection, it is the cylindrical portion of the coupler that interfaces with the handpiece that incorporates the proprietary design. This precludes the use of a universal replacement coupler for the coupler that utilizes a proprietary design The axis of the coupler and the axis of the handpiece are in substantial axial alignment (i.e. either substantially coaxial or substantially parallel). The end of the flexible supply connection is rigid, so that the flexible portion of the hose effectively begins a slight distance from the handpiece/coupler/supply interfaces. The result is that the end of the flexible supply or hose also is in substantial axial alignment with the coupler. The forces from the weight and flexural resistance of the hose are thus applied at a point well behind the area in which the dental professional grips the handpiece, resulting in a moment arm that increases the strain on the dental professional's hand. In addition to temporary fatigue and wrist strain from short periods of use, over long periods of time, this substantially continuous strain can lead to chronic problems such as carpal tunnel syndrome or other hand related problems.

What is needed is a coupler supply end interface that reduces the strain on the dental professional's hand, while still allowing the coupler supply end interface to meet the industry standard.

SUMMARY OF THE INVENTION

The present invention is a dental handpiece having an angled coupler. The coupler is positioned at the proximal end of the handpiece, so that air or water from a flexible supply mated to the angled coupler enters the handpiece substantially along the axis of the handpiece. The coupler may be integral with the handpiece or a coupler may be provided that is removable from the handpiece. The present invention, a dental handpiece having an angled coupler, may be used with both low speed dental air motors and high speed dental air motors having vane motors as well as with other handheld dental instruments such as dental scalers and dental handpieces driven by electric motors. The invention is not limited to vane-type air motors, as the invention can be used with dental handpieces having electric motors. However, the handpiece of the present invention is not configured to be used with turbine-type air motors.

The dental handpiece of the present invention comprises a proximal end, a distal end and a body between the proximal end and the distal end. The distal end has a head for attachment of a removable workpiece such as a dental burr or a disposable prophy-angle snap-on. The handpiece extends in a substantially axial direction from the distal end to the proximal end, although the head, which receives the removable workpiece, may extend from the distal end at an angle to the substantially axial direction. The handpiece body is positioned intermediate the proximal end and the distal end, the outer surface of the handpiece body forming a gripping surface conveniently located for the dental professional to comfortably grasp the body. The handpiece also serves to supply fluids or power of both originating from the proximal end. The fluids or power can be transported through one or more coordinates extending through the handpiece body. The proximal end of the handpiece further includes a coupling for providing a supply of material to preselected regions of the handpiece. This material typically includes water and air, but may also include an electrical conduit that supplies an electrical input for powering a handpiece with electrical requirements, while the fluids are supplied to preselected regions. For example, water may be provided through a conduit to the distal end of the handpiece for spraying a work area, while air may be supplied through a conduit either to be mixed with water to form a spray or to drive a vane motor or both. Electricity may be provided through a conduit to drive an electric motor, and a conduit may be used for a fiber optic to provide illumination capabilities. Thus, the handpiece can have a variety of conduits, depending upon its capabilities The handpiece also includes a coupler. The coupler includes a supply-end portion and a cylinder portion projecting from the supply-end portion. The cylinder portion of the coupler is assembled into the handpiece and is substantially aligned with the handpiece body, that is to say, it is either substantially coaxial with an axis of the handpiece, the handpiece axis extending from the proximal end through the handpiece body to the distal end, or it is substantially parallel to the handpiece axis. The supply-end portion of the coupler is angled with respect to the handpiece body so that fluids and power entering the handpiece body through the supply-end portion enters the handpiece body from the coupler cylinder portion substantially parallel to the axial direction of the handpiece body.

The supply-end portion of the coupler is configured to meet the requirements of the industry standard, ISO 9168. ISO 9168 specifies design standards for couplers of the present invention, referred to in ISO 9168 as connectors. As set forth in the Standard, a Type A coupler or connector includes 2 or 3 outlets; a Type B coupler or connector includes 4 or 5 outlets; a Type C coupler or connector has 4 outlets and electrical contacts; and, a Type D coupler or connector includes 3 outlets and a connection thread. The cylinder portion of the coupler includes a plurality of seals that, upon insertion of the cylinder portion into the handpiece body, isolate portions of the interior of the body so that fluid supplied to those portions of the body cannot be intermixed with fluid supplied to other portions of the body. The seals interface with the body to isolate portions of the handpiece body.

The coupler may be fabricated from metal, with the supply-end portion machined with a preselected angle. Alternatively, the coupler may include a metallic cylindrical section, and the supply-end portion may be molded onto the metallic cylindrical section and include an angled portion. The coupler may also be a separate coupling that has a first end and a second end, with an angle between the first end and the second end. The first end of the coupling attaches to the supply end of the coupler, while the second end of the coupling is configured to interface with the quick release feature on the flexible supply so that the handpiece-coupler-coupling combination can be readily removed from the flexible supply. The coupling serves as an adapter between the coupler and the flexible supply, incorporating the present invention into the coupling, permitting its use with handpieces utilizing a proprietary design for the coupler that prevents its replacement. In this circumstance, both the first end of the coupling and the second end of the coupling are configured in accordance with ISO 9168.

An advantage of the angled coupler is that the discomfort experienced by the dental professional is reduced. The weight of the hose is directed downward by the angled coupler at the coupler or coupling instead of along the flexible supply hose at a distance behind the coupler or coupling. The moment, which is the load multiplied by the distance, is reduced, resulting in a reduction in the discomfort.

Another advantage of the present invention is that side load exerted on the coupler is reduced. This, in turn, reduces the load exerted on the coupler seals in the cylindrical portion that isolate the water, air and optional electricity, which results in longer seal life.

Another advantage of the present invention is that the reduced load exerted on the coupler seals reduces the friction on the seals in handpieces designed to swivel. The reduced friction results not only in less seal wear but also easier rotation of the coupler.

Other features and advantages of the present invention will be apparent from the following more detailed description of the preferred embodiment, taken in conjunction with the accompanying drawings which illustrate, by way of example, the principles of the invention.

BRIEF DESCRIPTION OF THE DRAWINGS

Wherever possible, the same reference numbers will be used throughout the drawings to refer to the same or like parts.

DETAILED DESCRIPTION OF THE INVENTION

The handpiece assembly of the present invention modifies the proximal end of a dental handpiece so as to reduce the strain on the dental professional's hand. The proximal end of this handpiece is provided with a preselected angle. A flexible supply hose is attached to the proximal end so that bending of the supply hose in the region of the connection is minimized. In accordance with some current designs, the proximal end includes a swivel attachment to allow free rotation between the flexible supply and the coupler, usually at their interface. The preselected angle results in a reduction of the load resisting gravity in the attachment region. In addition to reducing the stress, the remaining load is applied closer to the handpiece resulting in a further reduction of moment, the moment being a product of the load and distance. The effect of the present invention is to reduce the applied load and to reduce the moment by moving the position of the resulting load closer to the grip area region, thus reducing the distance between the applied load and the gripping surface on the handpiece body. Although the overall load reduction experienced by the dental professional is slight, over the course of a day, the perceived fatigue reduction for the dental professional is significant.

Figure 1:
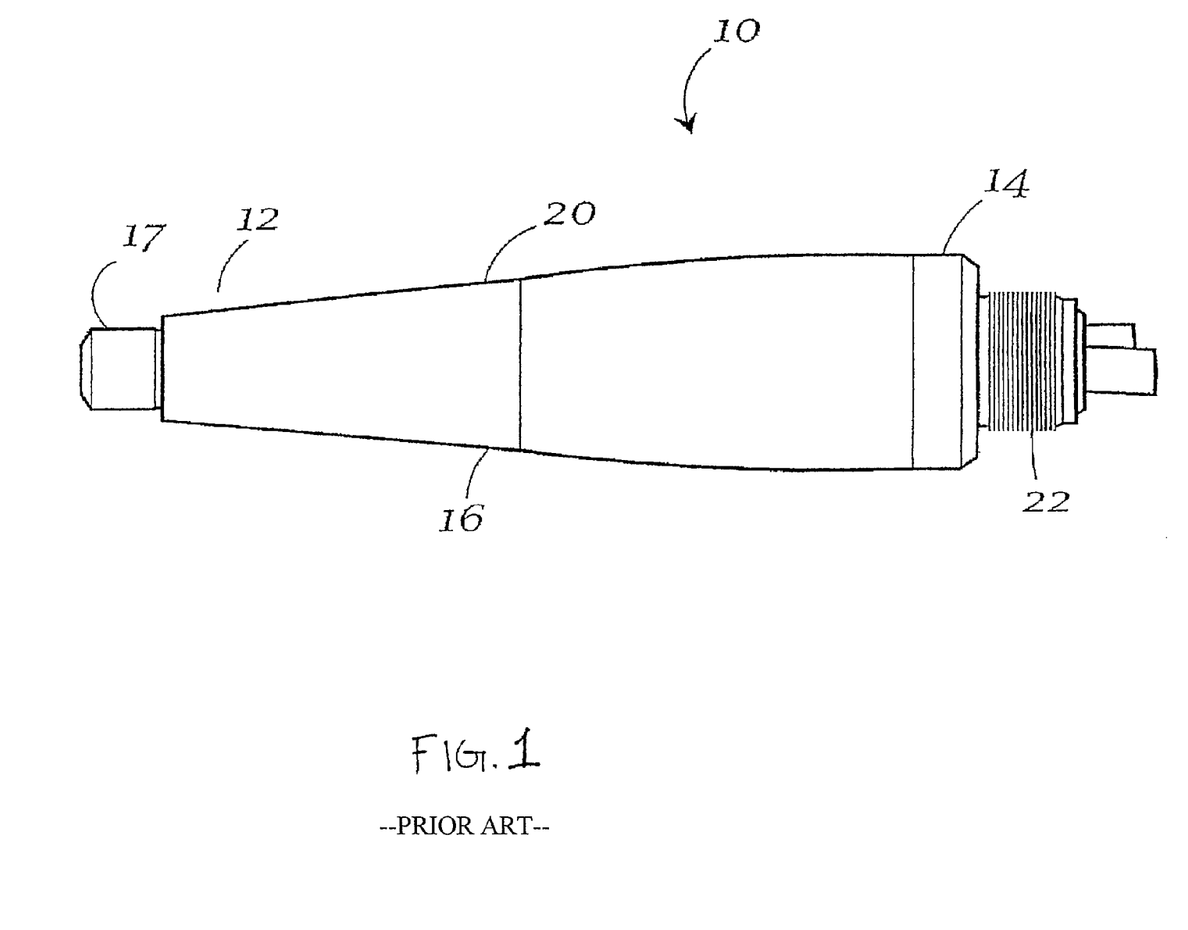
FIG. 1 depicts a commercially available handpiece with a coupler viewed substantially perpendicular to its axis.

FIG. 1 depicts a prior art commercially available dental handpiece 10. Handpiece includes a distal end 12, a proximal end 14 and a handpiece body 16 intermediate the proximal end 14 and the distal end 12. The proximal end 14, the handpiece body 16 and the distal end 12 are arranged in a substantially axial direction. Extending from the distal end 12 is a head attachment 17 onto which can be placed a head 18, not shown in FIG. 1, for performing a dental operation. The handpiece body 16 includes an ergonomically designed surface which serves as a gripping surface 20. A coupler 22 extends from the proximal end 14. Only a portion of the coupler 22 is visible in FIG. 1, as a portion of the coupler extending into the handpiece body 16 is not visible.

Figure 2:
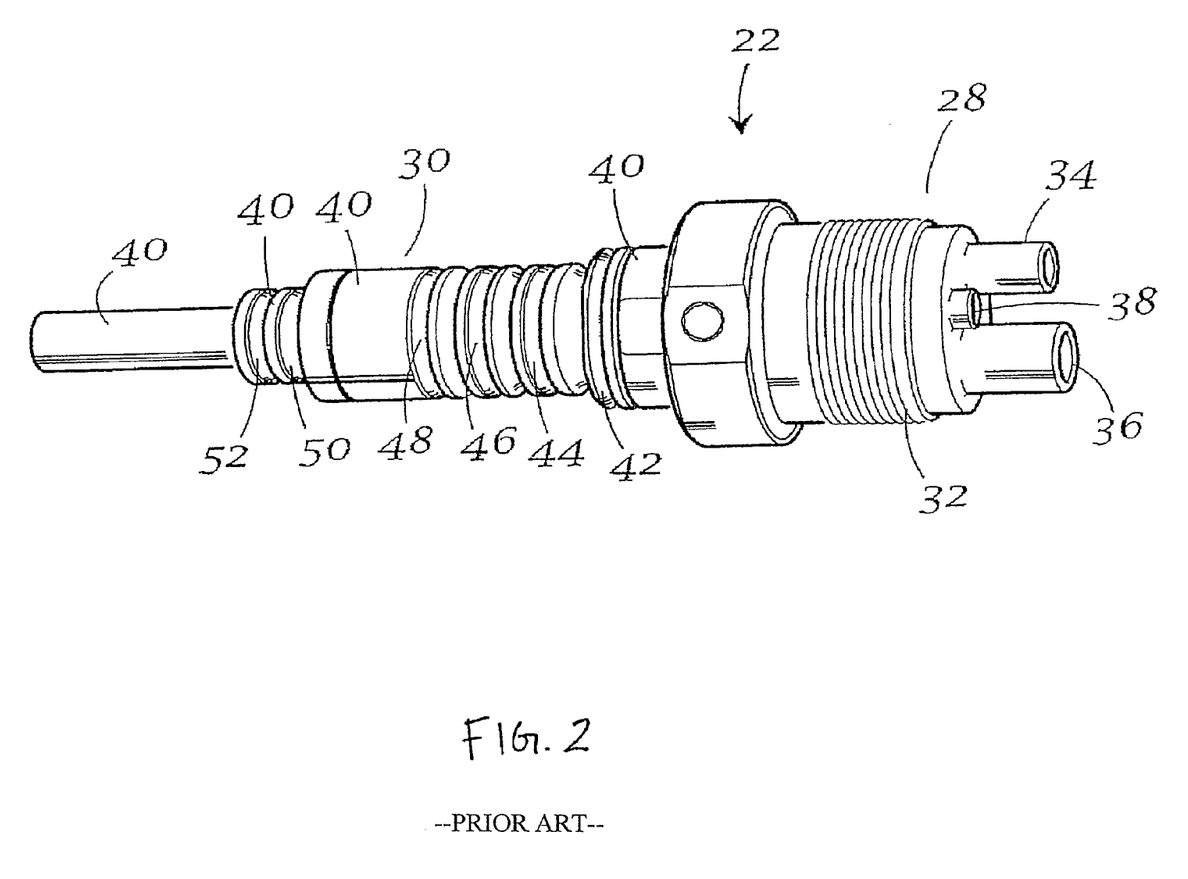
FIG. 2 depicts a commercially available coupler removed from its handpiece and viewed substantially perpendicular to its axis.

FIG. 2 depicts coupler 22, which includes a supply-end portion 28 and a cylinder portion 30 that projects from supply-end portion 28. Supply end portion is made in accordance with Industry Standards ISO 9168 and includes a threaded connection 32, as well as ports 34, 36 for air, port 38 for water and a port (not shown) acting as an electrical conduit. In this coupler, one of the ports 34, 36 may act as an air supply to drive a motor, while the other may serve as an exhaust for the air. Cylinder portion 30 of the coupler 22 includes a plurality of diameters 40, each isolated from an adjacent diameter by seals 42, 44, 46, 48, 50, 52. Cylinder portion 30 is assembled to handpiece body 16 so that seals 42, 44, 46, 48, 50, 52 interface with the inside surface of the handpiece body 16, thereby isolating portions of the interior of the handpiece body into chambers to prevent passage of fluid/material between or among chambers. The handpiece body 16 may also include vane motors or electric motors (not shown) to drive a workpiece such as a removable prophy-angle or burr. The cylinder portion can be inserted into handpiece body or the handpiece body can be molded around the cylinder portion (as well as other internals such as motors)

Figure 3:
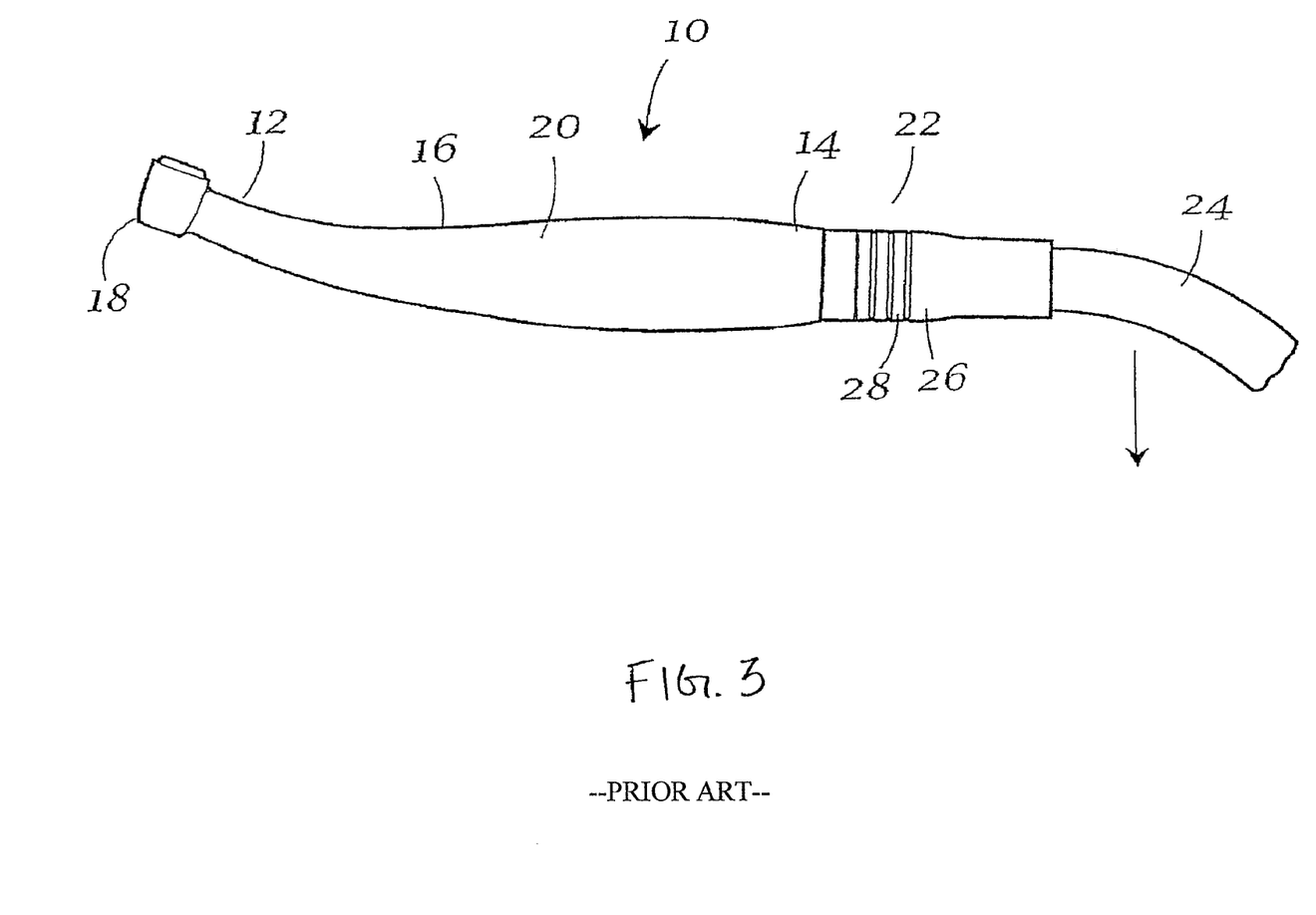
FIG. 3 is a view of a commercially available handpiece assembly having a distal end extending at a slight angle from its axis and mated to a flexible hose with a quick disconnect viewed substantially perpendicular to the axial direction.
Figure 4:
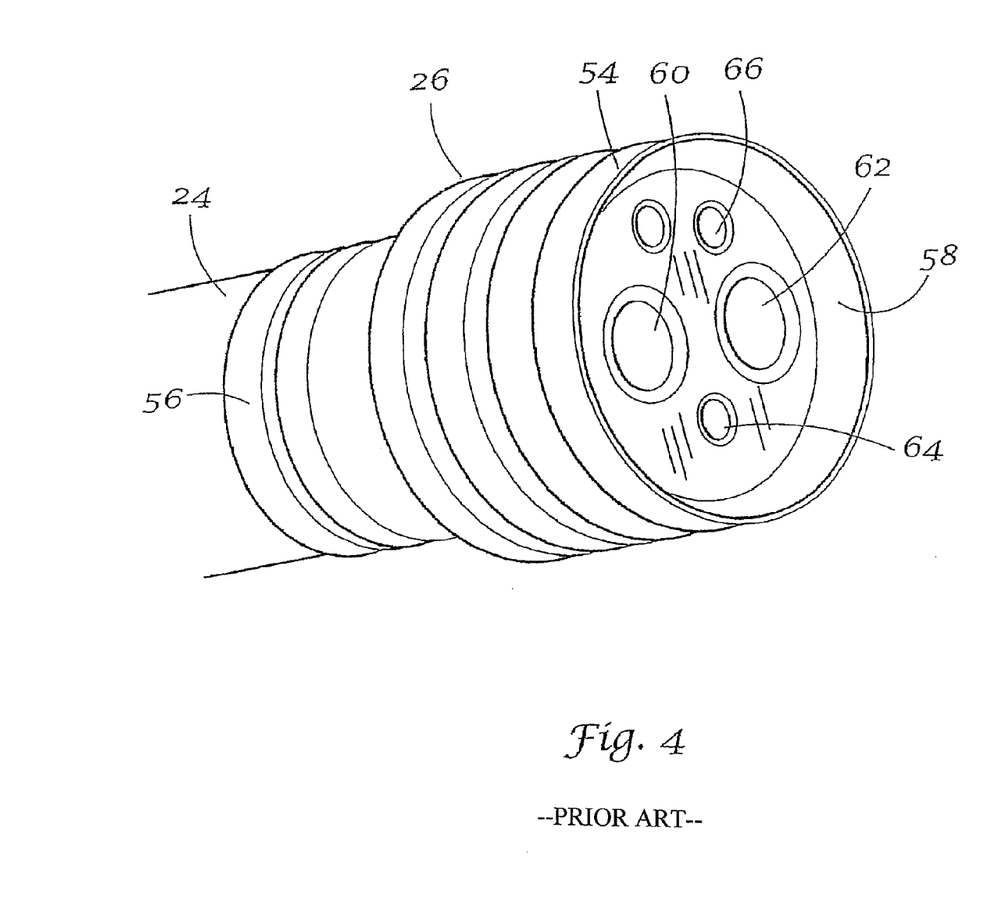
FIG. 4 is a perspective view of the first end of the quick disconnect of the commercially available handpiece assembly.

Once assembled into the handpiece body 16, the supply-end portion 28 of the coupler 22 extends in an axial direction from the handpiece body 16 as shown in FIG. 3. The flexible supply 24 is connected to the supply-end portion of the coupler 22 by a quick disconnect 26. The quick disconnect is depicted in FIGS. 3 and 4. A first end 54 of quick disconnect 26 that attaches to the handpiece assembly, either the handpiece 10 or assembled coupler 22 depending upon the design, is depicted. The second end 56 of quick disconnect 26 assembles to the flexible supply 24, in this embodiment the hose. Quick disconnect includes a connection 58 that mates with the connection on the handpiece assembly. Since this connection complies with ISO Standard 9168, it currently is a female thread arrangement. This thread mates with the male threaded connection 32 on the handpiece assembly, FIG. 2, depicted as extending from coupler 22 in this embodiment. However, other quick connect couplings are envisioned as ISO Standard 9168 evolves, the quick disconnect making the assembly of the handpiece to the flexible supply easier, but not otherwise affection the novel aspects of this invention. The quick disconnect includes air recesses 60, 62 to receive air ports 34, 36, a water recess 64 to receive water port 38 and an electrical passage 66 to act as an electrical conduit for wiring coupler 22 and handpiece 10. As an example, an electrical conduit may be inserted into this conduit. The quick disconnect depicted in FIG. 4 is in accordance with the current ISO Standard 9168 requirements.

In this handpiece 10, the head 18 is assembled over the head attachment 17 described in the prior art and the head may extend at an angle to the substantially axial arrangement of the proximal end 14, body 16 and distal end 18. It will be understood however, that head 18 can be arranged so that it also is aligned in a substantially axial direction with respect to the handpiece 10. In the assembly shown in FIG. 3, the portion of the assembly that includes quick disconnect 26, coupler 22 and a small portion of flexible hose, preferably up to about 1 centimeter, is rigid, even though coupler 22, which can include a swivel is free to rotate in body 16. The load effectively is located as shown by the downward arrow, in the best circumstance, where the rigidity ends, and may be further away from the quick disconnect along the flexible supply 24. The moment experienced by the dental professional is thus established by product of the weight of the handpiece 10, including the coupler 22, quick disconnect 26 and flexible supply 24 (at least along its region of rigidity) and the distance from the rigid section of supply 24 to the gripping surface 20.

As noted above, the present invention modifies the proximal end of the handpiece assembly so as to reduce the strain on the dental professional's hand. More specifically, the connection region that includes the proximal end of the handpiece, the coupler and the connection to the flexible supply, including a quick disconnect when provided, are modified to provide an angled input, while still maintaining a configuration at the interface that is in accordance with ISO Standard 9168.

Figure 5:
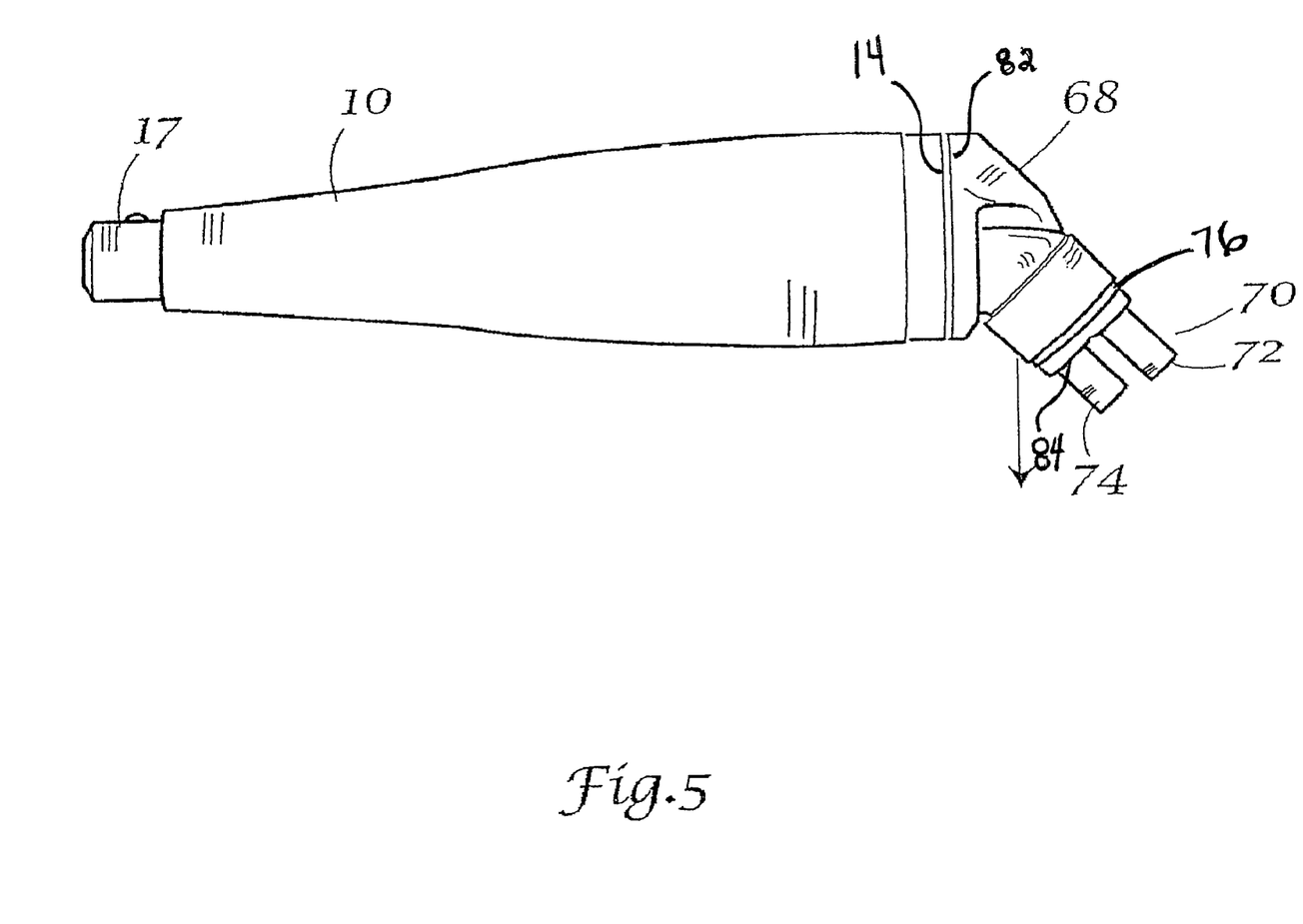
FIG. 5 is a view of a handpiece with an angled proximal end viewed substantially perpendicular to its axis.

FIG. 5 depicts one embodiment of the present invention with the proximal end 14 of the handpiece assembly being angled. The handpiece assembly of FIG. 5 includes a handpiece 10. Within handpiece 10, but not visible, is a coupler, substantially identical to coupler 22 depicted in FIG. 2. Depending on the handpiece design, the handpiece may also include a motor, such as an air motor or an electric motor, to drive a head that can be applied over the head attachment 17. In a variation of this embodiment, an angled joint 68 is affixed over the proximal end 14 of handpiece 10. Angled joint 68 can be molded onto the back end of the handpiece after the insertion of a motor and a coupler 22. Alternatively, angled joint 68 can be permanently glued onto the back end of the handpiece. In still another variation of this embodiment, angled joint 68 can be screwed onto the threaded portion of the coupler 22 or a threaded portion of the handpiece 10. It is also envisioned that the angled joint 68 can be manufactured integral with coupler 22, so that coupler 22 is a single piece of metal, such as aluminum or titanium (or their alloys). Angled joint 68 can be press fit, welded or otherwise permanently attached to handpiece 10. In this circumstance, the angled joint and/or coupler, once assembled, can only be factory disassembled. The angled joint 68 is angled downward at a preselected angle from the axis of the handpiece. The preselected angle can be any angle in the range of from about 10° to 90°, and preferably at an angle in the range of from 10° to 45°. It is important to note that the proximal end 70 of the angled joint 68 conforms to ISO Standard 9168. It is envisioned that the coupler selected will conform to Type A, Type B, Type C or Type D of ISO 9168, depending upon the outlets and electrical requirements of the handpiece. Air ports 72, 74 for air supply and exhaust are evident. In accordance with the Standard, an electrical conduit and a water port, although not shown in FIG. 5, are also present. The proximal end 70 includes a threaded connection 76, and is thus configured to accept a standard quick disconnect 26 that conforms to ISO Standard 9168.

As noted, a variation of this embodiment can utilize a coupler 22 machined so that the supply-end portion is angled with respect to the axis of the cylinder portion.

Figure 6:
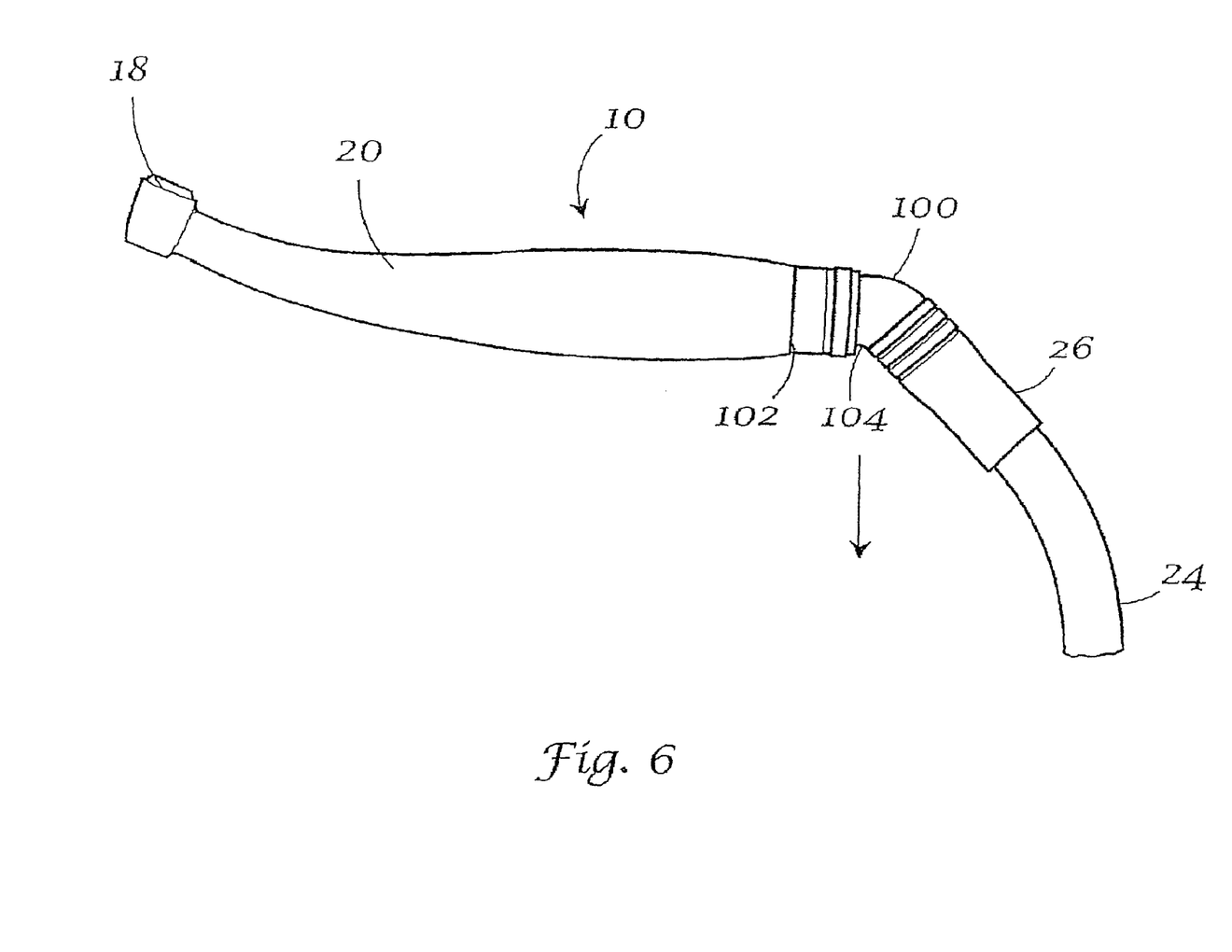
FIG. 6 is a view of handpiece assembly with an angled coupling between the handpiece and the quick disconnect viewed substantially perpendicular to its axis.

Referring to FIG. 5 and FIG. 6, the fluid and electrical supplied to the handpiece body are input through the proximal end of the angled joint 70 or to the coupler front end 84 at an angle to the axis of the handpiece body 10, but are provided to the proximal end of the handpiece body 10 at the coupler second end 82 substantially in the axial direction. This is an important feature, since a vane motor housed substantially in the vicinity of the distal end of the handpiece is powered by the supplied air. In order to achieve proper operation of such a motor, the air must impinge the motor in an axial direction.

The quick disconnect 26, upon connection to angled joint 68 results in the flexible supply being directed in a downward direction. Thus, the load is reduced as the extra weight resulting from the quick disconnect and the portion of the flexible supply immediately adjacent to the quick disconnect is directed downward by the angled joint 68, as shown by the downward arrow. Additionally, the flexural resistance of the flexible supply 24 to the stresses of downward bending are reduced if not completely removed. Finally, the moment is reduced, because the distance from the effective point where the load is directed downward to the gripping surface of the handpiece is shortened, being moved from a point along the flexible supply 24 to the angled joint.

A second embodiment of the present invention is depicted in FIG. 6. This embodiment utilizes a coupling 100 intermediate the quick disconnect 26 and the handpiece 10. Coupling 100 is a separate independent piece. Coupling 100 has a first end 102 and a second end 104, being connected to the handpiece assembly on a first end 102 and to a quick disconnect 26 on a second end 104, there being an angular transition at a preselected angle between the coupling first end 102 and coupling second end 104. The second end 104 of coupling made in accordance to ISO Standard 9168 for assembly to quick disconnect 26, also conforming to ISO Standard 9168. Thus, the second end of coupling 104 is configured substantially identically to the supply-end portion of coupler 22 depicted in FIG. 2, while the first end of coupling 102 is configured substantially identically to the first end 54 of the quick disconnect of FIG. 4.

The quick disconnect assembles to the second end 104 of coupling 100, while the first end 102 of coupling assembles to the handpiece assembly, thereby allowing fluids and electrical power to enter, and as appropriate, leave, the proximal end of the handpiece body in an axial direction, as discussed above. The advantage to coupling 100 is that it is adaptable to any handpiece assembly design, since both the first end 102 and second end 104 are configured in accordance with ISO Standard 9168. This permits a dental professional utilizing a handpiece having a proprietary design to gain the advantage of the reduced loads and moment aim of the present invention without having to replace the entire handpiece. Since all current handpiece assemblies have a proximal end configured in accordance with ISO Standard 9168, so that either the handpiece 100 itself or the coupler 22 matingly conforms to a quick disconnect 26. The coupling 100 can be retrofitted to handpiece assemblies in order to reduce the strain experienced by the dental professional. A coupling 100 can be provided conforming to Type A, Type B, Type C or Type D of ISO Standard 9168, depending upon the outlets and electrical requirements of the handpiece.

In a variation of the second embodiment, the angled portion between the coupling first end 102 and second end 104 is movable. As used herein, the term "movable" means that the angled portion can be changed from one fixed angle to another fixed angle, or the angled portion can be articulating so that its movement automatically adjusts with the user, the angle constantly changing as the user moves handpiece 10 from between 10° and 90°, preferably between 10° and 45°. When the angled portion can be changed from a first fixed angle to a second fixed angle, a means for fixing that fixes the angle in a position is released and the angle is changed to the second fixed angle, after which the means for fixing is reengaged. The means for fixing can be any release/locking mechanism such as a key/keyhole, a twist mechanism, a ball in a detent, a spring release mechanism etc. The angled portion can be changed to one of a plurality of angles between 10° and 90°. If the angled portion has an articulating movement, so that it automatically adjusts with user movement, the design may be a ball and socket arrangement or other equivalent mechanical design.

In a third embodiment of the invention, a quick disconnect has a first end for attachment to a handpiece assembly and a second end for attachment to a flexible supply 24. The quick disconnect includes an angle between the first end and a second end. The first end and the second end of the quick disconnect otherwise conform to ISO Standard 9168. Again, the angle can be movable from moved from a first fixed angle to a second fixed angle, or the angle in the quick disconnect can be articulating, the angles varying from about 10° to 90°, preferably varying from 10° to 45°. One of the distinctions between the first embodiment and the second embodiments, discussed above, and this third embodiment is that the distance between the gripping surface and the effective load point is moved back further from the gripping surface so that the moment, while reduced, is not reduced as much as in the first and second embodiment, since the distance, while shortened, is not reduced as much as in previous embodiments.

The present invention reduces the perceived discomfort experienced by the dental professional. The overall stress is reduced, since the flexural stress contribution from the flexible supply 24 is substantially reduced. Furthermore the moment experienced by the user is reduced since both the overall load is reduced and the moment arm is shortened. The load contribution for the flexible supply has already been discussed. The moment arm in prior art handpieces extends from the gripping surface 20 to a portion of the flexible supply where the load is directed in a substantially downward direction. The moment arm of the present invention is shortened so that it extends from the gripping surface to substantially the proximal end 14 of the handpiece. Since the moment is the product of the moment arm multiplied by the load, it is apparent that since both of these are reduced, the moment arm is also substantially reduced.

As noted above, the flexural stresses on the hose are reduced, resulting in a reduced moment. In addition, the reduction of the flexural stresses also can result in reduced fatigue on the hose. The constant manipulation of the hose by the dental professional can result in degradation of the hose by fatigue over a period of time. By reducing the flexural stresses, degradation of the hose by fatigue will also be reduced, and a longer hose life will result.

In addition to the above improvements, the side load between the handpiece 10 and the coupler will also be reduced. The flexural stresses from the hose are balanced by a load being applied between the coupler and the handpiece, which load is applied at the points of contact between the coupler and handpiece. Those points of contact are seals 42-52. By reducing the flexural stresses in the flexible supply, the load between the seals and the handpiece are also reduced, resulting in longer seal life. For swivel couplers, the reduction in load will also mean a reduction in wear between the seals and the handpiece body due to decreased friction. This further contributes to extended seal life in swivel couplers.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A dental assembly comprising:
a dental handpiece, the dental handpiece having a proximal end, a distal end, the distal end including an attachment for assembly of a removable workpiece;

a handpiece body intermediate the proximal end and the distal end, the handpiece body having a gripping surface;

the handpiece extending in a substantially axial direction along an axis, the axis including a portion of the distal end, the handpiece body and a portion of the proximal end;

a coupler that includes at least a first portion extending in an axial direction, the first portion interfaces with an interior of the body to isolate portions of the body interior into at least one distinct chamber;

a coupling unit having a first portion and a second portion, the first portion of the coupling unit being substantially coaxial with the handpiece body and the second portion of the coupling unit angled with respect to the handpiece axis, the second portion further including a fitting, the coupling unit including a plurality of conduits, the at least one distinct chamber in fluid communication with one of the conduits of the plurality of conduits;

a generally flexible hose, the flexible hose having a hose connector with a hose fitting for attachment to the coupling fitting, wherein the hose includes separate supply lines for providing fluids to the handpiece through the conduits; and wherein the conduits transport the fluids from the hose, through the coupling unit and coupler to the handpiece; and wherein the hose fitting being attached to the second portion of the coupling unit at a movable angle, the movable angle is selectable from a preselected first fixed angle to a second preselected fixed angle in a range from 10° to 90°; and wherein at least one of the interfacing hose fitting and coupling unit fitting are a quick disconnect fitting to facilitate assembly of the hose to the coupling unit; and wherein the proximal end includes a swivel attachment to allow free rotation of the flexible hose.

2. The dental handpiece of claim 1, wherein the handpiece body further includes a motor.

3. The dental handpiece of claim 2 wherein the coupler further comprising a supply-end portion which includes an outlet having electrical contacts.

4. The dental handpiece of claim 3 wherein the motor in the handpiece body is an electric motor in communication with the electrical contacts at the supply-end portion.

5. The dental handpiece of claim 3 wherein the motor in the handpiece body is a vane-type air motor in communication with the outlet in the supply-end portion that provides drive air.

6. The dental assembly of claim 1 wherein the first portion of the coupling unit is housed in the handpiece body and the first portion of the coupling unit is assembled over the coupler, the coupling unit being connected to the handpiece body.

7. The dental assembly of claim 1 wherein the coupler further includes a second portion opposed to the first portion of the coupler, the second portion of the coupler extending in an axial direction away from the handpiece body and wherein first portion of the coupling unit is removably connected to the second portion of the coupler.

8. The dental assembly of claim 1 wherein the generally flexible hose further provides electricity to the handpiece and at least one of the conduits of the plurality of conduits further includes electrical contacts in communication with the hose to provide electricity to the handpiece.

9. The dental assembly of claim 1 wherein the coupling unit is an articulating coupling unit.

10. The dental assembly of claim 1 wherein the second portion of the coupling unit is an articulating coupling with respect to the first portion of the coupling unit.

11. The dental handpiece of claim 1, wherein upon movement of the supply-end portion of the coupler to a preselected angle, the supply-end portion is angled relative to the handpiece axis so that the flexural resistance to the stresses of downward bending of a flexible supply attached to the supply-end portion of the coupler are reduced.

* * * * *